United States Patent [19]

Spitzer

[11] 3,954,731

[45] May 4, 1976

[54] PROCESS FOR PREPARING 6-ALKOXYPENICILLANIC AND 7-ALKOXYCEPHALOSPORIN ACIDS

[75] Inventor: Wayne A. Spitzer, Indianapolis, Ind.

[73] Assignee: Eli Lilly and Company, Indianapolis, Ind.

[22] Filed: Oct. 4, 1973

[21] Appl. No.: 403,697

Related U.S. Application Data

[63] Continuation-in-part of Ser. No. 268,362, July 3, 1972, abandoned.

[52] U.S. Cl.......................... 260/239.1; 260/243 C; 424/246; 424/271
[51] Int. Cl.²............... C07D 499/04; C07D 501/04
[58] Field of Search...................... 260/243 C, 239.1

[56] References Cited
UNITED STATES PATENTS

| | | | |
|---|---|---|---|
| 3,819,621 | 6/1974 | Morimoto et al. | 260/243 C |
| 3,842,072 | 10/1974 | Heusler et al. | 260/243 C |

Primary Examiner—Paul M. Coughlan, Jr.
Attorney, Agent, or Firm—William B. Scanlon; Everet F. Smith

[57] ABSTRACT

6-Acylamido-6-lower alkylthio (benzylthio) penicillanic and 7-acylamido-7-lower alkylthio (benzylthio)cephalosporanic and deacetoxycephalosporanic acid esters are reacted at a temperature between −80° and −25°C. with one equivalent of halogen to provide an intermediate halosulfonium halide which is reacted with a $C_1$–$C_4$ lower alcohol, benzyl alcohol, p-nitrobenzyl alcohol or 2,2,2-trichloroethanol in the presence of a hydrogen halide acceptor to provide the corresponding 6- or 7- O-alkyl, benzyl, p-nitrobenzyl or 2,2,2-trichloroethyl penicillanic, cephalosporanic or deacetoxycephalosporanic acid esters. The 6- and 7- (2,2,2-trichloroethoxy) substituted penicillin or cephalosporin is reacted with zinc in formic acid to provide the 6- or 7-hydroxypenicillin or cephalosporin respectively.

9 Claims, No Drawings

PROCESS FOR PREPARING 6-ALKOXYPENICILLANIC AND 7-ALKOXYCEPHALOSPORIN ACIDS

CROSS-REFERENCE

This application is a continuation-in-part of co-pending application Ser. No. 268,362 filed July 3, 1972, now abandoned.

BACKGROUND OF THE INVENTION

Since the prediction by Strominger, *Amer. J. Med.*, 39, 708 (1965), that 6-methylpenicillins and 7-methylcephalosporins should have an enhanced antimicrobial activity; and the recent discovery of the naturally occurring 7-methoxycephalosporins, R. Nagarajan, et al., *J. Amer. Chem. Soc.*, 93, 2308 (1971), considerable interest has developed in the synthesis of β-lactam antibiotics bearing a substituent in the position α to the β-lactam carbonyl of the penicillin and cephalosporin antibiotics.

In copending application Ser. No. 268,358, filed July 3, 1972, now abandoned, the preparation of 6-acylamido-6-lower alkylthiopenicillanic acids, 7-acylamido-7-lower alkylthiocephalosporanic acids and 7-acylamido-7-lower alkylthiodeacetoxycephalosporanic acids is described. The present invention relates to a process for converting the thio substituted penicillins and cephalosporins described therein to 6-alkoxy substituted penicillins and 7-alkoxy substituted cephalosporins.

SUMMARY OF THE INVENTION

A 6-acylamido-6-lower alkylthiopenicillin or a 7-acylamido-7-lower alkylthiocephalosporin is allowed to react with one equivalent of halogen in an inert solvent at a temperature between about −80° and about −25°C. to provide the corresponding halosulfonium halide. The halosulfonium group is displaced with a lower alcohol, for example, methanol, in the presence of a hydrogen halide acceptor, for example, a tertiary amine such as triethylamine, to provide by displacement a 6-alkoxypenicillin or a 7-alkoxycephalosporin.

The alkoxylated penicillins and cephalosporins provided by the process of this invention have useful antibiotic activity, and can be employed to combat infections caused by the gram positive and gram negative microorganisms.

DETAILED DESCRIPTION

The present invention provides a process for the conversion of 6-lower alkylthio (benzylthio)-6-acylamidopenicillins and 7-lower alkylthio (benzylthio)-7-acylamidocephalosporins to the corresponding acylamido 6- and 7-lower alkoxy, 2,2,2-trichloroethoxy, benzyloxy, and p-nitrobenzyloxy, substituted compounds. The conversion of the S-alkyl β-lactam substituted compounds to the O-alkyl β-lactam substituted compounds is carried out by reacting the S-alkyl compounds with halogen to provide the halosulfonium halide, for example, the chlorosulfonium chloride, which is then reacted in the presence of a base with a lower alkyl alcohol, 2,2,2-trichloroethanol, benzyl alcohol, or p-nitrobenzyl alcohol to provide the alkoxylated β-lactam compound.

According to the process of this invention a 6-acylamido-6-alkylthio or benzylthio substituted penicillin ester or a 7-acylamido-7-alkylthio or benzylthio cephalosporin ester represented by the Formula I.

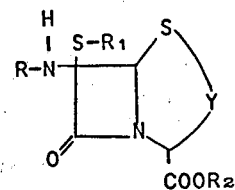

I wherein
R is an acyl group;
$R_1$ is $C_1$-$C_4$ lower alkyl or benzyl;
$R_2$ is carboxylic acid protecting ester forming group; and
Y is

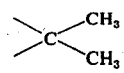

or

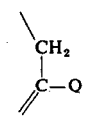

wherein Q is methyl or acetoxy methyl; is reacted in an inert solvent at a temperature between about −80° and about −25° C. wih bromine or chlorine to provide a halosulfonium halide represented by the formula II

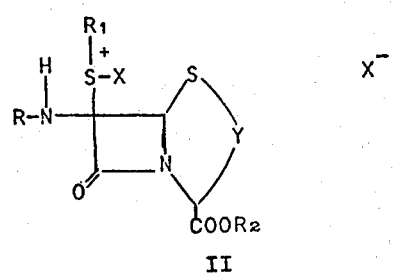

II wherein X is chloro or bromo and R, $R_1$, $R_2$, and Y have the same meanings as defined in Formula I. To the cold reaction mixture containing the halosulfonium halide is added an excess of an alcohol represented by the formula

$R_3OH$ wherein $R_3$ represents $C_1$—$C_4$ lower alkyl, 2,2,2-trichloroethyl, benzyl or p-nitrobenzyl, with one equivalent of a base or a hydrogen halide acceptor. Following the addition of the alcohol, $R_3OH$, and the base or hydrogen halide acceptor the reaction mixture is maintained in the cold for about 10 minutes to about 30 minutes with stirring. Thereafter the reaction mixture is allowed to warm to room temperature and the reaction product a 6-acylamido-6-alkoxylated penicillin ester of a 7-acylamido-7-alkoxylated cephalosporin ester represented by the Formula III is recovered from the reaction mixture.

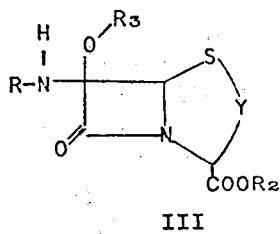

III wherein R, $R_2$, $R_3$, and Y have the same meanings as defined above.

In the foregoing description of the process of this invention the term, R, represents an acyl group which can be any of a wide variety of acyl groups which have previously been described as the acyl moiety of the side chains of known penicillins and cephalosporins. For example R can be a $C_1$–$C_7$ alkanoyl group such as acetyl, propionyl, valeryl and the like, a haloalkanoyl group for example chloroacetyl, bromoacetyl, 2-chloropropionyl, and the like; an aroyl group, for example, benzoyl, α-naphthoyl, substituted benzoyl for example 2,6-dimethoxybenzoyl, p-nitrobenzoyl, 4-methylbenzoyl, 4-hydroxybenzoyl, 4-chlorobenzoyl, 3,4-dichlorobenzoyl, 4-bromobenzoyl, and the like; an alkanoyl group substituted by a phenyl ring or a heterocyclic ring and which group may bear a substituent α to the carbonyl, for example phenylacetyl, phenoxyacetyl, α-aminophenylacetyl, α-hydroxyphenylacetyl, 2-thienylacetyl, 3-thienylacetyl, 2-furylacetyl, phenylmercaptoacetyl, and the like groups wherein the aromatic ring portion is substituted by hydroxy, chloro, bromo, lower alkyl, or methoxy, such as 4-chlorophenylacetyl, 3-hydroxyphenoxyacetyl, 3-bromophenylacetyl, 3-hydroxyphenylglycyl, 4-hydroxymandeloyl, and the like acyl groups. The nature of the acyl group, R, is not critical in the present process so long as such acyl group is unreactive with the halogens bromine and chlorine. However, acyl groups having a divalent sulfur atom attached to two aliphatic carbon atoms are generally undesirable as a side chain group of the starting penicillin or cephalosporin ester since such sulfur groups can compete with the 6- and 7-alkylthio groups in the reaction with halogen.

The 6-acylamido-6-alkylthio (or benzylthio)penicillin esters and the 7-acylamido-7-alkylthio (or benzythio) cephalosporin esters represented by the Formula I, the starting materials in the present process, are prepared according to the process described in copending U.S. patent application Ser. No. 268,358. According to this method an ester of 6-APA, 7-ACA, or 7-ADCA is reacted with a benzaldehyde, for example p-nitrobenzaldehyde, to provide the 6- or 7-p-nitrobenzylidene amino derivative thereof. The imine derivative is then reacted in an inert solvent at a temperature of about −80° to about 0° C. with a strong base such as lithium diisopropyl amide or sodium hydride to generate the anionic form of the imine, which is then reacted with a $C_1$–$C_4$ lower alkoxycarbonyl $C_1$–$C_4$ lower alkyl (or benzyl) disulfide for example, methoxycarbonylmethyl disulfide or ethoxycarbonylbenzyl disulfide, to provide the 6- and 7-alkylthiolated or benzylthiolated imine. The substituted imine ester is then reacted with a carbonyl reagent for example Girard's Reagent T or aminooxyacetic acid to afford the substituted amino β-lactam ester. The 6-amino-6-alkylthiopenicillin ester or the 7-amino-7-alkylthiocephalosporin ester is then acylated in the conventional manner to provide a compound of the Formula I. For example, 2,2,2-trichloroethyl 7-ACA is reacted with p-nitrobenzaldehyde in ethanol to afford the trichloroethyl ester of 7-(p-nitrobenzylidene)aminocephalosporanic acid. The imine ester is then reacted with sodium hydride or lithium diisopropyl amide to generate the anionic form of the imine which is then reacted with methoxycarbonylmethyl disulfide to provide the 7-methylthio substituted imine ester. The substituted imine ester is reacted with Girard's Reagent T or other suitable carbonyl reagent for example aminooxyacetic acid or phenylhydrazine, to provide the substituted amino ester, 7-amino-7-methylthiocephalosporanic acid trichloroethyl ester. The free amino nucleus is acylated in a conventional manner to provide the desired 7-acylamido-7-methylthiocephalosporanic acid ester. Accordingly, such process provides a wide variety of 6- and 7- alkyl(benzyl) thio penicillins and cephalosporins.

The term, "a carboxylic acid protecting ester forming group", as used herein refers to such groups as are commonly employed in the penicillin and cephalosporin art to protect the respective carboxylic acid functions of the penicillin and cephalosporin molecule. Illustrative of such groups which can be used are the benzyl, p-nitrobenzyl, 4-methoxybenzyl, 3,5-dimethoxybenzyl, diphenylmethyl, 2,2,2-trichloroethyl, t-butyl, phenacyl, tetrahydropyranyl, and the like carboxylic acid protecting groups. The function of such ester forming groups, as are represented by $R_2$ in the Formula I, is not critical in the present process and such groups serve merely to protect the carboxylic acid function so as to prevent its completion with the chlorination and displacement reaction of the present process.

Inert solvents which can be employed in the preparation of the intermediate halosulfonium halides (Formula II) includes solvents which are generally unreactive towards the halogens and in which the starting penicillins and cephalosporin esters or at least partially soluble. Solvents which can be employed include the chlorinated hydrocarbon solvents such as chloroform, methylene dichloride, and tetrachloroethylene. Methylene chloride is a preferred solvent of the present invention.

In the halogenation of an alkylthio compound of the Formula I, one equivalent or a slight excess of one equivalent of the halogen is employed. Commonly a solution of one equivalent of the halogen, chlorine or bromine, in the inert solvent for example methylene chloride is added to a solution of the alkylthio compound in methylene chloride or other inert solvent at the reaction temperature of about −80° to about −25° C. After the addition of the halogen the reaction mixture is stirred in the cold for about 10 minutes to insure formation of the sulfonium halide. Thereafter one equivalent of a base or hydrogen halide acceptor is added with an excess of the alcohol, $R_3OH$, required to form the desired alkoxy β-lactam compound of the Formula III.

Compounds which can function as the base or hydrogen halide acceptor in the present process include the hydrogen halide acceptors such as the tertiary organic amines trimethylamine, triethylamine, pyridine, the collidines, lutidines, the picolines, quinoline, iso-quinoline, the N,N-dialkylanilines, such as N,N-dimethylaniline, N,N-diethylaniline the highly hindered secondary amines such as diisopropyl amine, dicyclohexylamine, and the like; and bases, for example, the alkali metal hydroxides, carbonates, and bicarbonates such as sodium hydroxide, potassium hydroxide, sodium carbonate, sodium bicarbonate, potassium carbonate and the like, the alkali metal alcoholates such as sodium methylate, sodium ethylate, potassium ethylate and the like. Alkylene oxides such as ethylene oxide and propylene oxide can also function as the hydrogen halide acceptor.

One equivalent of the hydrogen halide acceptor or base is added to the reaction mixture containing the halosulfonium halide, followed by the addtion of an excess of the alcohol, $R_3OH$. Alternatively one equivalent of the hydrogen halide acceptor is dissolved in an excess amount of the alcohol, $R_3OH$, and the solution is added to the reaction mixture of the halosulfonium halide. The alkali metal hydroxides, carbonates, and bicarbonates are desirably added as solutions or partial solutions in the alcohol, $R_3OH$. One equivalent of the base is employed and desirably an excess of the alcohol is added.

The alcohols represented by the formula, $R_3OH$, which can be employed in the present process include the $C_1$–$C_4$ lower alkyl alcohols such as methanol, ethanol, n-propanol, n-butanol, the branched lower alkyl carbinols such as iso-propanol, sec-butanol, and the like; and the carbinols 2,2,2-trichloroethanol, benzyl alcohol, and p-nitrobenzyl alcohol.

Following the addition of the base or the hydrogen halide acceptor and the alcohol, the reaction mixture is stirred at the reaction temperature for about 5 to about 30 minutes and is thereafter allowed to warm to a temperature of about 20° to 25° C. The reaction product, a 6-alkoxy or a 7-alkoxy β-lactam compound represented by the Formula III is recovered from the reaction product mixture by extraction and chromatography. For example the reaction mixture is diluted with a saturated solution of sodium chloride and the product extracted from the diluted mixture with a suitable solvent for example methylene chloride or ethyl acetate. The extract is washed and dried and thereafter is evaporated to yield the crude reaction product. The crude product can be purified by preparative thin layer chromatography when small amounts of the products are obtained, or by column chromatography when larger quantities are prepared. The chromatography is desirably carried out over a silica gel adsorbent.

Following the isolation and purification of the reaction product, a 6-alkoxy-6-acylamidopenicillanic acid ester or a 7-alkoxy-7-acylamidocephalosporin ester, the product is reacted by known hydrolysis or hydrogenolysis procedures to affect removal of the ester group to provide the product in the free acid form. For example, the benzyl, diphenylmethyl, p-nitrobenzyl and 3,5-dimethoxybenzyl groups represented by $R_2$ can be removed by hydrogenolysis, for example, by reacting the ester with hydrogen in the presence of 10 percent palladium on carbon catalyst in an inert solvent. The 2,2,2-trichloroethyl group is removed by reacting the ester with zinc and formic or glacial acetic acid. Other known carboxylic acid protecting groups which can be employed are removed by known methods.

In a preferred embodiment of the present process a solution of 2,2,2-trichloroethyl 6-phenoxyacetamido-6-thiomethylpenicillanate in methylene chloride is cooled to a temperature of $-76°$ C. and a solution of one equivalent of chlorine in methylene chloride is added to the cold solution. The reaction mixture is stirred for about ten minutes and a solution of one equivalent of triethylamine in an excess of ethanol is added to the reaction mixture with stirring. The reaction mixture is agitated for approximately ten minutes and is then allowed to warm to room temperature with stirring. The reaction mixture is evaporated, and the residue is chromatographed over silica gel. Multiple fractions are collected and those fractions containing one spot material, as demonstrated by thin layer chromatography of each fraction, are combined and are evaporated to yield the reaction product, 2,2,2-trichloroethyl 6-ethoxy-6-phenoxyacetamidopenicillanate. The ethoxy β-lactam ester is then reacted with zinc in formic acid to effect the cleavage of the trichloroethyl ester group and provide the penicillanic acid.

In carrying out the above process certain of the conditions and reactants are preferred over others. In the preparation of the halosulfonium halide intermediate the preferred halogen is chlorine and the preferred inert solvent is methylene chloride. The preferred hydrogen halide acceptor is triethylamine.

Preferred alkylthio and benzylthiopenicillin and cephalosporin starting materials are represented by the following formula

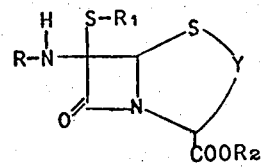

wherein
R is $C_2$–$C_7$ alkanoyl, benzoyl, $C_1$–$C_4$ lower alkylbenzoyl, halobenzoyl, $C_1$–$C_4$ lower alkoxybenzoyl, nitrobenzoyl, hydroxybenzoyl, or a group of the formula

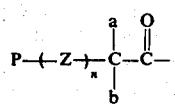

wherein
P is phenyl, $C_1$–$C_4$ lower alkylphenyl, halophenyl, $C_1$–$C_4$ lower alkoxy phenyl, nitrophenyl, hydroxyphenyl, or a heteromonocyclic radical containing O, S, and/or N;
Z is O or S;
n is 0 or 1
a is hydrogen or $C_1$–$C_3$ lower alkyl;
b is hydrogen, $C_1$–$C_3$ lower alkyl, hydroxy, amino or protected amino;
$R_1$ and $R_2$ have the same meanings as defined above for Formulae I;

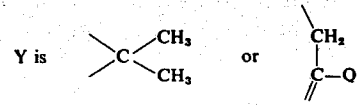

wherein Q is methyl or acetoxymethyl.

The term "protected amino", refers to an amino group substituted by one of the commonly employed amino blocking groups such as t-butyloxycarbonyl, benzyloxycarbonyl, 2,2,2-trichloroethoxycarbonyl, phthaloyl and like groups.

Illustrative of the groups represented by R in Formula I are the following: phenylacetyl, phenoxyacetyl, benzoyl, 2,6-dimethoxybenzoyl, 4-nitrophenylacetyl, 3-hydroxyphenylacetyl, 4-methylphenoxyacetyl, 2-thienylacetyl, 2-furylacetyl, 3-pyridylacetyl, 2-oxazolylacetyl, 2-thiazolylacetyl, 2,2-dimethylphenylacetyl, mandeloyl, 3-hydroxymandeloyl, phenylglycyl, 4-chlorophenylacetyl, phenylmercaptoacetyl, 2-thienylmercaptoacetyl, 2-pyranylacetyl, 2-pyridylacetyl, 2-oxazolylacetyl, 3-furylacetyl, 2-(1,3,4-thiadiazolyl)acetyl, 4-bromophenylmercaptoacetyl, 2-imidazolylacetyl, 5-pyrimidylacetyl, 3,4-dichlorophenylacetyl, 4-hydroxyphenylmercaptoacetyl and like acyl groups.

In the foregoing definition the term, "$C_2$–$C_7$ alkanoyl", refers to acetyl, propionyl, butyryl, iso-butyryl, pivaloyl, valeryl, n-hexanoyl, n-heptanoyl and like groups. The term, "$C_1$–$C_4$ lower alkyl", has reference to methyl, ethyl, n-propyl, iso-propyl, n-butyl, t-butyl, and the like. The term, "$C_1$–$C_4$ lower alkylbenzoyl", refers to 4-methylbenzoyl, 4-iso-propylbenzoyl, 4-t-butylbenzoyl, 3,4-dimethylbenzoyl, 3-ethylbenzoyl, 2-methylbenzoyl and the like; "$C_1$–$C_4$ lower alkoxybenzoyl" refers to 2,6-dimethoxybenzoyl, 4-ethoxybenzoyl, 3-iso-propoxybenzoyl, 3-ethoxy-4-methoxybenzoyl, 3,4-dimethoxybenzoyl and the like; "nitrobenzoyl" refers to 4-nitrobenzoyl, 3-nitrobenzoyl and the like; "halobenzoyl" is defined herein as the mono or dihalogenated benzoyl groups such as 4-fluorobenzoyl, 3-chlorobenzoyl, 3,4-dichlorobenzoyl, 3-bromobenzoyl and the like; and "hydroxybenzoyl" is defined by such groups as 4-hydroxybenzoyl, 3,4-dihydroxybenzoyl, 2,4-dihydroxybenzoyl, 3-hydroxybenzoyl and the like.

The term "heteromonocyclic radical containing O, S, and/or N" as employed herein refers to the 5 and 6 membered heterocyclic groups of one ring such as 2-thienyl, 3-thienyl, 2-furyl, 3-furyl, 2-oxazolyl, 2-thiazolyl, triazinyl, tetrazolyl, 2-imidazolyl, 1,3,4-oxadiazolyl, 1,3,4-thiadiazolyl, 2-pyridyl, 3-pyridyl, pyrimidyl, pyrazinyl, 3-pyrryl, pyranyl, piperidyl, and the like.

Representative of the group, —S—$R_1$, are methylthio, ethylthio, n-propylthio, iso-propylthio, n-butylthio, benzylthio and the like.

Illustrative of the starting materials which can be employed are the following:

6-[2'-(2-furyl)acetamido]-6-methylthiopenicillanic acid,
7-(2'-amino-2'-phenylacetamido)-7-methylthiodeacetoxycephalosporanic acid,
7-(2'-hydroxy-2'-phenylacetamido)-7-methylthiocephalosporanic acid,
7-(2'-amino-2'-phenylacetamido)-7-methylthiocephalosporanic acid.
7-[2'-(2-thienyl)acetamido]-7-methylthiocephalosporanic acid,
7-(2'-hydroxy-2'-phenylacetamido)-7-benzylthiodeacetoxycephalosporanic acid,
7-(2'-amino-2'-phenylacetamido)-7-ethylthiocephalosporanic acid,
6-(2,6-dimethoxybenzamido)-6-methylthiopenicillanic acid,
7-(4-hydroxyphenylacetamido)-7-n-propylthiodeacetoxycephalosporanic acid,
7-(4-chlorophenoxyacetamido)-7-methylthiocephalosporanic acid,
7-phenoxyacetamido-7-iso-propylthiocephalosporanic acid,
7-[2'-(3-thienyl)acetamido]-7-n-butylthiodeacetoxycephalosporanic acid,
6-(2',2'-dimethyl-2'-phenylacetamido)-6-methylthiopenicillanic acid,
7-[2'-(2-s-triazinyl)acetamido]-7-methylthiodeacetoxycephalosporanic acid,
7-[2'-(1,3,4-thiadiazol-2yl)acetamido]-7-methylthiodeacetoxycephalosporanic acid,
7-[2'-(1,3,4-oxadiazol-2yl)acetamido]-7-ethylthiocephalosporanic acid,
6-[2'-amino-2'-(4-hydroxyphenyl)acetamido]-6-isopropylthiopenicillanic acid,
7-acetamido-7-benzylthiocephalosporanic acid,
7-(2'-pyranylacetamido)-7-methylthiocephalosporanic acid,
7-(2'-piperidylacetamido)-7-methylthioacetoxycephalosporanic acid,
7-(5'-oxazolylacetamido)-7-methylthiodeacetoxycephalosporanic acid,
6-phenylacetamido-6-methylthiopenicillanic acid,
7-phenoxyacetamido-7-methylthiodeacetoxycephalosporanic acid, and the like.

The compounds represented by the Formula III wherein $R_3$ is 2,2,2-trichloroethyl, benzyl or p-nitrobenzyl are useful intermediates in the preparation of the correspondingly substituted 6- and 7-hydroxy-$\beta$-lactam antibiotics.

Accordingly, in a further aspect of the present invention a 6-acylamidopenicillanic acid or a 7-acylamidocephalosporanic or deacetoxycephalosporanic acid, represented by the Formula III wherein $R_3$ is benzyl, p-nitrobenzyl, or 2,2,2-trichloroethyl, is reacted under either catalytic hydrogenolysis conditions or with zinc and formic acid to provide the correspondingly substituted 6-hydroxy and 7-hydroxypenicillin and cephalosporin compounds represented by the formula IV

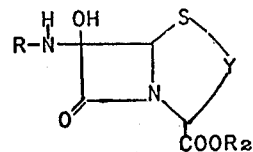

IV wherein R and Y have the same meanings as defined above, and $R_2$ is hydrogen or a carboxylic acid protecting ester forming group as defined for Formulae I, II and III. A preferred group of compounds represented by IV are those compounds wherein R is the preferred acyl group as previously described for the starting materials, the acylamido thio substituted penicillin and cephalosporin esters.

When $R_3$ is a 2,2,2-trichloroethyl group the corresponding hydroxy compound of the Formula IV is prepared by reacting the trichloroethoxy substituted compound with zinc in the presence of formic acid or glacial acetic acid. This reaction is carried out under the conditions employed for the cleavage of a 2,2,2-trichloroethyl ester derivative of a penicillin or cephalosporin. When $R_3$ is a benzyl or p-nitrobenzyl group, the preparation of the compound of Formula IV is carried out by the catalytic hydrogenolysis of IV in an inert solvent in the presence of a supported palladium catalyst, for example 10 percent palladium supported on activated carbon. The hydrogenolysis is carried out in a solvent such as ethyl acetate, dimethylformamide, ethanol, and like inert solvents, at a temperature between about 25° and 45° C. The amount of catalyst employed is variable, however, an amount in excess of the amounts commonly used for hydrogenolysis reactions is desirable. For example, 10 percent of the weight of the substrate compound affords the best results. The hydrogenolysis proceeds slowly and reaction times of approximately 12 hours are required. Catalysts which can be employed are palladium on carbon, palladium on aluminum, palladium on silica gel, palladium on barium carbonate and the like. Following the hydrogenolysis, the reaction mixture is filtered to remove the catalyst and the filtrate is diluted with water. The hydroxylated product of the Formula IV is recovered from the diluted filtrate by extraction with solvents such as ethyl acetate, methylene chloride, or chloroform. The extract is washed and dried and is then evaporated to provide the crude reaction product mixture containing the hydroxylated penicillin or cephalosporin. The product is obtained in a purified form by chromatography. Preparative thin layer chromatography on silica gel affords the purified hydroxy compounds when small amounts of the compound are prepared. When larger scale reactions are carried out, column chromatography over silica gel is employed.

When both $R_2$ and $R_3$ of the Formula III are the same, and represent a trichloroethyl group, a benzyl group, or a p-nitrobenzyl group, the above described cleavage reaction for the group $R_3$ will also result in the cleavage of the ester forming group $R_2$ to provide directly the acid form of the hydroxy compound. Likewise when $R_2$ is any group capable of catalytic hydrogenolysis and $R_3$ is the p-nitrobenzyl group, or the benzyl group, the ester group $R_2$ will likewise be removed concurrently with the group $R_3$.

The halosulfonium halides represented by the Formula II are relatively stable substances under the conditions described above for their preparation. Although the halosulfonio group,

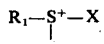

wherein $R_1$ and X are as described above, for example the chloromethylsulfonio group

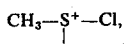

is a labile group the sulfonium halides of the Formula II can be isolated if desired. However, in the present process it is preferable to prepare and react the sulfonium halides in situ.

Illustrative of the halosulfonium halides of the Formula II which are useful as intermediates for preparing the compounds of Formula III are the following. In the naming of the compounds which follow, an abbreviated nomenclature system is employed for convenience. The group

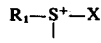

is referred to as a haloalkylsulfonio substituent at the $C_6$ of a penicillin compound or at the $C_7$ of a cephalosporin compound. According to the Chemical Abstracts nomenclature system the compound represented by the Formula II,

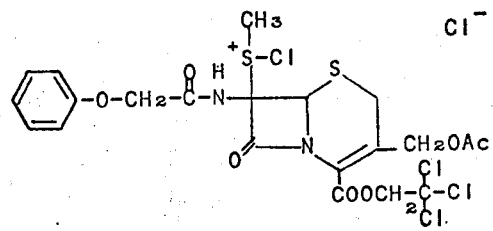

is named [3-(acetoxymethyl)-2-(2,2,2-trichloroethoxycarbonyl)-7-(2-phenoxyacetamido)-5-thia-1-azabicyclo[4.2.0] octane-7-yl] chloromethylsulfonium chloride. The above compound is named herein as 2,2,2-trichloroethyl 7-phenoxyacetamido-7-chloromethylsulfoniocephalosporanate chloride. The following exemplary compounds are named likewise: 2,2,2-trichloroethyl 6-phenylacetamido-6-chloromethylsulfoniopenicillanate chloride, p-nitrobenzyl 6-phenoxyacetamido-6-bromomethylsulfoniopenicillanate bromide, 2,2,2-trichloroethyl-6-[2'-(2-thienyl)acetamido]-6-chloromethylsulfoniopenicillanate chloride, benzyl 6-acetamido-6-chloroethylsulfoniopenicillanate chloride, 2,2,2-trichloroethyl 7-phenoxyacetamido-7-chloromethylsulfoniocephalosporanate chloride, 2,2,2-trichloroethyl 7-[2'-(2-thienyl)acetamido]-7-chloromethylsulfoniodeacetoxycephalosporanate chloride, p-nitrobenzyl 7-phenoxyacetamido-7-chloroisopropylsulfoniodeacetoxycephalosporanate chloride, diphenylmethyl 7-[2'-(2-thienyl)acetamido]-7-chloromethylsulfoniocephalosporanate chloride, p-nitrobenzyl 6-(2,6-dimethoxybenzamido)-6-bromomethylsulfoniopenicillanate bromide, 2,2,2-trichloroethyl 7-(2'-hydroxyphenylacetamido)-7-chloroethylsulfoniodescetoxycephalosporanate chloride, 2,2,2-trichloroethyl 7-(2'-aminophenylacetamido)-7-chlorobenzylsulfoniodeacetoxycephalosporanate chloride, p-nitrobenzyl 6-acetamido-6-chloro-n-propylsulfoniopenicillanate chloride, 2,2,2-trichloroethyl 7-acetamido-7-bromoethylsulfoniopenicillanate chloride, 2,2,2-trichloroethyl 7-acetamido-7-bromoethylsulfoniocephalosporanate bromide and like penicillin and cephalosporin sulfonium halide esters.

Representative of the compounds provided by this invention are the following:
 6-acetamido-6-methoxypenicillanic acid,
 6-propionamido-6-methoxypenicillanic acid,
 6-phenoxyacetamido-6-iso-propoxypenicillanic acid,
 6-[2'-(2-thienyl)acetamido]-6-methoxypenicillanic acid
 6-phenylacetamido-6-methoxypenicillanic acid,
 6-phenoxyacetamido-6-ethoxypenicillanic acid,
 6-phenoxyacetamido-6-ethoxypenicillanic acid, 6-phenoxyacetamido-6-benzyloxypenicillanic acid,
6-phenylacetamido-6-p-nitrobenzyloxypenicillanic acid,
6-phenoxyacetamido-6-(2,2,2-trichloroethoxy)-penicillanic acid,
6-acetamido-6-(2,2,2-trichloroethoxypenicillanic acid
6-(2'-hydroxyphenylacetamido)-6-methoxypenicillanic acid
6-(2'-aminophenylacetamido)-6-methoxypenicillanic acid,
6-(2'-(3-thienyl)acetamido-6-methoxypenicillanic acid,
6-(2,6-dimethoxybenzamido)-6-methoxypenicillanic acid,
6-benzamido-6-n-butoxypenicillanic acid,
6-(4-hydroxybenzamido)-6-methoxypenicillanic acid,
7-acetamido-7-methoxycephalosporanic acid,
7-propionamido-7-methoxydeacetoxycephalosporanic acid,
7-valeramido-7-methoxydeacetoxycephalosporanic acid,
7-valeramido-7-methoxycephalosporanic acid,
7-benzamido-7-methoxycephalosporanic acid,
7-benzamido-7-ethoxycephalosporanic acid,
7-(2,6-dimethoxybenzamido)-7-methoxydeacetoxycephalosporanic acid,
7-phenylacetamido-7-methoxycephalosporanic acid,
7-p-chlorophenylacetamido-7-n-propoxycephalosporanic acid,
7-p-nitrophenylacetamido-7-methoxydeacetoxycephalosporanic acid,
7-phenoxyacetamido-7-methoxycephalosporanic acid,
7-phenoxyacetamido-7-methoxydeacetoxycephalosporanic acid,
7-[2'-(2-thienyl)acetamido]-7-methoxycephalosporanic acid,
7-[2'-(3-thienyl)acetamido]-7-ethoxydeacetoxycephalosporanic acid,
7-chloroacetamido-7-benzyloxycephalosporanic acid,
6-[2'-(2-thienyl)acetamido]-6-hydroxypenicillanic
6-phenoxyacetamido-6-hydroxypenicillanic acid,
6-phenylmercaptoacetamido-6-hydroxypenicillanic acid,
6-(2,6-dimethoxybenzamido)-6-hydroxypenicillanic acid,
6-(4-chlorophenylmercaptoacetamido)-6-hydroxypenicillanic acid,
7-phenoxyacetamido-7-hydroxycephalosporanic acid,
7-phenoxyacetamido-7-hydroxydeacetoxycephalosporanic acid,
7-[2'-(2-thienyl)acetamido]-7-hydroxycephalosporanic acid,
7-phenylacetamido-7-hydroxydeacetoxycephalosporanic acid,
7-(2'-aminophenylacetamido)-7-hydroxycephalosporanic acid,
7-(2'-hydroxyphenylacetamido)-7-hydroxydeacetoxycephalosporanic acid,
7-(2'-aminophenylacetamido)-7-hydroxydeacetoxycephalosporanic acid,
7-(2'-pyranylacetamido)-7-methoxydeacetoxycephalosporanic acid,
7-[2'-(oxazol-2-yl)acetamido]-7-methoxycephalosporanic acid,
7-[2'-(1,3,4-thiadiazo-2-yl)acetamido]-7-methoxycephalosporanic acid,
7-[2'-(2-pyridyl)acetamido]-7-methoxydeacetoxycephalosporanic acid,
7-[2'-(2-pyrryl)acetamido]-7-methoxydeacetoxycephalosporanic acid,
7-[2'-(oxazol-2-yl)acetamido]-7-ethoxycephalosporanic acid,
7-[2'-(oxazol-2-yl)acetamido]-7-hydroxycephalosporanic acid,
7-[2'-tetrazol-2-yl)acetamido]-7-methoxycephalosporanic acid,
7-bromoacetamido-7-methoxydeacetoxycephalosporanic acid,
7-[2'-(2furyl)acetamido]-7-methoxycephalosporanic acid
7-phenoxyacetamido-7-(2,2,2-trichloroethoxy)-deacetoxycephalosporanic acid,
7-phenylmercaptoacetamido-7-methoxycephalosporanic acid,
7-p-chlorophenylmercaptoacetamido-7-methoxydeacetoxycephalosporanic acid,
7-(2'-hydroxyphenylacetamido)-7-methoxycephalosporanic acid,
7-(2'-aminophenylacetamido)-7-methoxydeacetoxycephalosporanic acid,
7-(2'-aminophenylacetamido)-7-p-nitrobenzyloxydeacetoxycephalosporanic acid,
7-(2'-aminophenylacetamido)-7-(2,2,2-trichloroethoxy)deacetoxycephalosporanic acid, and like penicillanic, cephalosporanic and deacetoxycephalosporanic acids, the carboxylic acid protecting ester derivatives thereof, and the pharmaceutically acceptable salts thereof.

Certain of the substituted penicillins and cephalosporins provided by the process of this invention are described and claimed in copending applications Ser. Nos. 222,294 filed Jan. 31, 1972, and 222,293, filed Jan. 31, 1972, both now abandoned. The β-lactam antibiotics described above which have a 2,2,2-trichloroethoxy group in the 6- and 7- positions of the penicillin and cephalosporins compounds respectively are novel compounds which are useful for the preparation of the correspondingly substituted 6- and 7-hydroxy penicillin and cephalosporin compounds. The 6-alkoxypenicillins, 6-benzyloxypenicillins, 7-alkoxycephalosporins and 7-benzyloxycephalosporins possess antibiotic activities and are useful in combatting infections due to gram positive and gram negative organisms. Accordingly the products of the present process can be parenterally administered in a suitable non-toxic dose to an infected host in the treatment of such infections. In general the compounds can be administered at a dose between about 50 and 500 mg/kg of body weight. Substantial variation in dosage regimen may be required depending upon such conditions as the general physical condition of the host, the severity of the infection; the locus of the infection and the particular organism responsible for the infection. For example, a single daily dose may suffice with a particular host while the others, multiple doses spaced throughout the day may be required to achieve the desired response.

According to the above described aspects of the present invention there is provided a process for converting 6-alkylthio- or 6-benzylthio penicillins and the 7-alkylthio-or 7-benzylthiocephalosporins represented by the Formula I to the correspondingly substituted 6-alkoxy, benzyloxy, p-nitrobenzyloxy, or trichloroethoxy penicillins and the similarly 7-substituted cephalosporins represented by the Formula III; the halo sulfonium halide intermediates represented by the Formula II useful in the above described process; and the 6-hydroxypenicillins and the 7-hydroxy cephalosporins represented by the Formula IV above.

The following detailed examples further illustrate the present invention.

EXAMPLE 1

2,2,2Trichloroethyl 6-phenoxyacetamido-6-methoxypenicillanate

To a solution of 480 mg. (0.91 mmole) of 2,2,2-trichloroethyl 6-phenoxyacetamido-6-thiomethylpenicillanate in 20 ml. of methylene chloride maintained at a temperature of −76° C. by means of a dry ice-acetone bath was added with stirring 81 ml. of a solution of chlorine in methylene chloride (1 mmole of chlorine per ml). The reaction mixture was stirred for 10 min and a solution of 0.91 mmole of sodium methylate in 20 ml. of methanol was added. The reaction mixture was allowed to warm to room temperature and 200 ml. of a saturated solution of sodium chloride were added. The mixture was then extracted with 200 ml. of methylene chloride and the extract was dried and evaporated. The residue was chromatographed on a preparative silica gel thin layer chromatogram to give 3 major fractions. Fractions 1 and 2, 95 mg, were combined and identified as 2,2,2-trichloroethyl 6-phenoxyacetamido-6-methoxypenicillnate.

Nmr: δ CDCl$_3$; 1.55(s,6,—CH$_3$), 3.56 (s,3,—O—CH$_3$), 4.60 (s,2,—CH$_2$), 4.82 (s,2,—CH$_2$), 5.68 (s, 1,C$_5$—H), 6.82–7.66 (m,6, phenyl and NH).

EXAMPLE 2

2,2,2-Trichloroethyl 6-ethoxy-6-phenoxyacetamidopenicillante

To a solution of 555 mg. of 2,2,2-trichloroethyl 6-phenoxyacetamido-6-thiomethylpenicillanate in 10 ml. of methylene chloride maintained at a temperature of −76° C. was added with stirring 105 ml. of a solution of chlorine in methylene chloride at a concentration of 1 mmole of chlorine per ml. After 10 minutes a solution of 100 mg. of triethylamine in 10 ml. of ethanol was added to the reaction mixture. The reaction mixture was stirred for 10 minutes and was then allowed to warm to room temperature. The reaction mixture was evaporated and the residue chromatographed on a silica gel thin layer chromatogram. The one spot material, which was shown on development, was collected and extracted from the silica with methylene dichloride. The extract was evaporated to dryness to yield 225 mg. of 2,2,2-trichloroethyl 6-ethoxy-6-phenoxyacetamidopenicillanate as confirmed by its nuclear magnetic resonance spectrum. Mass spectrometry gave a parent ion of 524.

EXAMPLE 3

2,2,2-Trichloroethyl 6-iso-propoxy-6-phenoxyacetamidopenicillanate

Following the reaction conditions and procedures described in Example 2, 475 mg. of 2,2,2-trichloroethyl 6-phenoxyacetamido-6-thiomethylpenicillanate was reacted with chlorine and the intermediate chloromethylsulfonium chloride was reacted with isopropanol in the presence of triethylamine to provide, after separation and purification by thin layer chromatography, 89 mg. of 2,2,2-trichloroethyl 6-iso-propoxy-6-phenoxyacetamidopenicillanate as confirmed by its nuclear magnetic resonance spectrum.

There was also isolated from the above reaction product mixture by thin layer chromatography, 2,2,2-trichloroethyl 6-hydroxy-6-phenoxyacetamidopenicillanate as shown by the nuclear magnetic resonance spectrum of a sample of the isolated compound.

EXAMPLE 4

2,2,2-Trichloroethyl 7-[2'-(2-thienyl)acetamido]-7-methoxycephalosporanate.

Following the procedures described in Example 2, 2,2,2-trichloroethyl 7[2'-(2-thienyl)acetamido]-7-thiomethylcephalosporanate is reacted with one equivalent of chlorine in methylene chloride at −76° C. to provide 2,2,2-trichloroethyl 7-[2'-(2-thienyl)acetamido]-7-chloromethylsulfoniocephalosporanate chloride. To the cold reaction mixture is added a solution of one equivalent of triethylamine in methanol and after 15 minutes the reaction mixture is allowed to warm to room temperature to provide 2,2,2-trichloroethyl 7-[2'-(2-thienyl)acetamido]-7-methoxycephalosporanate.

EXAMPLE 5 p-Nitrobenzyl 6-p-nitrobenzyloxy-6-phenylacetamidopenicillanate

Following the reaction procedures described in Example 2, p-nitrobenzyl 6-thioethyl-6-phenylacetamidopenicillanate is reacted with chlorine in methylene chloride to afford p-nitrobenzyl 6-chloroethylsulfonio-6-phenylacetamidopenicillanate chloride which product is reacted with p-nitrobenzyl alcohol in the presence of one equivalent of triethylamine to provide p-nitrobenzyl 6-p-nitrobenzyloxy-6-phenylacetamidopenicillanate.

EXAMPLE 6

2,2,2-Trichloroethyl 7-thiobenzyl-7-phenoxyacetamidodeacetoxycephalosporanate is reacted with one equivalent of bromine in methylene chloride at a temperature of −75°C. and the 2,2,2-trichloroethyl 7-bromobenzylsulfonio-7-phenoxyacetamidodeacetoxycephalosporanate bromide formed is reacted with ethanol in the presence of one equivalent of triethylamine to produce 2,2,2-trichloroethyl 7-ethoxy-7-phenoxyacetamidodeacetoxycephalosporanate.

EXAMPLE 7

2,2,2-Trichloroethyl 7-thiomethyl-7-phenoxyacetamidodeacetoxycephalosporanate is reacted at a temperature of −75° C. in methylene chloride with one equivalent of chlorine and the chloromethylsulfonium chloride formed is reacted with 2,2,2-trichloroethanol in the presence of one equivalent of triethylamine to provide, 2,2,2-trichloroethyl 7-phenoxyacetamido-7-(2,2,2-trichloroethoxy)deacetoxycephalosporanate.

EXAMPLE 8

The trichloroethyl ester reaction product of Example 7 is reacted with a suspension of zinc (5–10 gram atom excess) in 90% formic acid at a temperature of about 25°C. and the reaction mixture is diluted with brine. The diluted mixture is extracted with ethyl acetate and the extract is washed with a dilute solution of sodium bicarbonate, water, and is dried. The dried extract is evaporated to dryness to provide, 7-hydroxy-7-phenoxyacetamidodeacetoxycephalosporanic acid sodium salt. The salt is dissolved in a mixture of water and ethyl acetate and the solution is acidified with dilute hydrochloric acid. The ethyl acetate layer is separated, is washed with water and is dried. The dried extract is evaporated to dryness to provide 7-hydroxy-7-phenoxyacetamidodeacetoxycephalosporanic acid.

EXAMPLE 9

Following the reaction conditions and procedures of Examples 6 and 7, 2,2,2-trichloroethyl 6-thiomethyl-6-phenylacetamidopenicillanate is reacted with chlorine and the chloromethylsulfonium chloride product is reacted with excess 2,2,2-trichloroethanol in the presence of one equivalent of triethylamine to provide 2,2,2-trichloroethyl. 6-phenylacetamido-6-(2,2,2-trichloroethoxy)penicillanate. The product is reacted with zinc in 90% formic acid to provide 6-hydroxy-6-phenylacetamidopenicillanic acid.

EXAMPLE 10

Following the procedures and conditions described in Examples 6 and 7, the following compounds are prepared:
  6-acetamido-6-hydroxypenicillanic acid,
  6-hydroxy-6-[2'-(2-thienyl)acetamido]penicillanic acid,
  6-hydroxy-6-(2,6-dimethoxybenzamido)penicillanic acid,
  7-hydroxy-7-[2'-(2-thienyl)acetamido]deacetoxycephalosporanic acid,
  7-hydroxy-7-[2'-(2-thienyl)acetamido]cephalosporanic acid,
  7-hydroxy-7-(2'-hydroxyphenylacetamido)deacetoxycephalosporanic acid,
  7-hydroxy-7-(2'-aminophenylacetamido)deacetoxycephalosporanic acid, and the like.

I claim:
1. The method for preparing an alkoxylated β-lactam ester of the formula

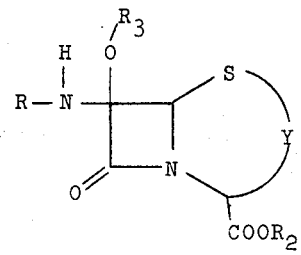

wherein R is $C_2$–$C_7$ alkanoyl, benzoyl, $C_1$–$C_4$ lower alkylbenzoyl, halobenzoyl, $C_1$–$C_4$ lower alkoxybenzoyl, nitrobenzoyl, hydroxybenzoyl, or a group of the formula

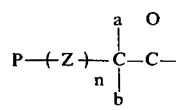

wherein P is phenyl, $C_1$–$C_4$ lower alkylphenyl, halophenyl, $C_1$–$C_4$ lower alkoxyphenyl, nitrophenyl, hydroxyphenyl, or a heteromonocyclic radical containing O, S, and/or N selected from the group consisting of thienyl, furyl, 2-oxazolyl, 2-thiazolyl, triazinyl, tetrazolyl, 2-imidazolyl, 1,3,4-oxadiazolyl, 1,3,4-thiadiazolyl, 2-pyridyl, 3-pyridyl, pyrimidyl, pyrazinyl, 3-pyrryl, pyranyl and piperidyl; Z is O or S;

$n$ is 0 or 1;
  $a$ is hydrogen or $C_1$–$C_3$ lower alkyl; and
  $b$ is hydrogen, $C_1$–$C_3$ lower alkyl, hydroxy, t-butyloxycarbamido, benzyloxycarbamido, 2,2,2-trichloroethoxycarbamido or phthalimido;
  $R_2$ is a carboxylic acid protecting ester forming group;
  $R_3$ is $C_1$–$C_4$ lower alkyl, benzyl, p-nitrobenzyl or 2,2,2-trichloroethyl; and
  Y is the 3-carbon fragment

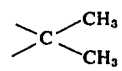

or the substituted 2-carbon fragment

wherein Q is methyl or acetoxymethyl; which comprises the steps of
  a. halogenating with chlorine or bromine in an inert solvent a thio substituted β-lactam ester compound of the formula

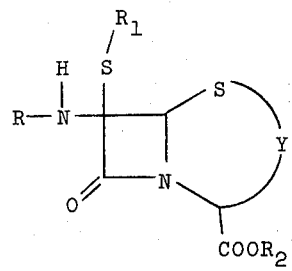

wherein $R_1$ is $C_1$–$C_4$ lower alkyl or benzyl, and R, $R_2$ and Y are as defined above, at a temperature between —80° and —25° C. to form the β-lactam halosulfonium halide of the formula

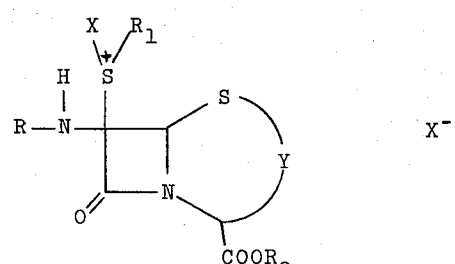

wherein R, $R_1$, $R_2$ and Y are as defined above and X is chloro or bromo;

b. adding to said halogenation mixture maintained at a temperature between −80° and −25° C. one equivalent of a hydrogen halide acceptor and at least one molar equivalent of the alcohol $R_3OH$, wherein $R_3$ is $C_1$–$C_4$ lower alkyl, benzyl, p-nitrobenzyl, or 2,2,2-trichloroethyl; and c. recovering said alkoxylated β-lactam ester.

2. The method of claim 1 wherein $R_1$ is methyl.

3. The method of claim 1 wherein Y is the 3-carbon fragment

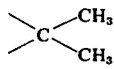

4. The method of claim 1 wherein Y is the substituted 2-carbon fragment

5. The method of claim 3 wherein the thio substituted β-lactam ester is 2,2,2-trichloroethyl 6-phenoxyacetamido-6-thiomethylpenicillanate.

6. The method of claim 3 wherein the thio substituted β-lactam ester is 2,2,2-trichloroethyl 6-thioethyl-6-phenoxyacetamido penicillanate.

7. The method of claim 3 wherein the thio substituted β-lactam ester is 2,2,2-trichloroethyl 6-thio-isopropyl-6-phenoxyacetamidopenicillanate.

8. The method of claim 4 wherein the thio substituted β-lactam esters is 2,2,2-trichloroethyl 7-thiomethyl-7-phenoxyacetamidodeacetoxycephalosporanate.

9. The method of claim 1 wherein $R_3$ is 2,2,2-trichloroethyl.

* * * * *